United States Patent [19]
Fauquex et al.

[11] Patent Number: 5,990,289
[45] Date of Patent: Nov. 23, 1999

[54] METHOD FOR THE PURIFICATION OF PROTEINS

[75] Inventors: Pierre François Fauquex, Basel; Catherine Georges, Aesch, both of Switzerland

[73] Assignee: Novartis AG, Basel, Switzerland

[21] Appl. No.: 09/000,031

[22] PCT Filed: Jul. 17, 1996

[86] PCT No.: PCT/EP96/03144

§ 371 Date: Jan. 20, 1998

§ 102(e) Date: Jan. 20, 1998

[87] PCT Pub. No.: WO97/05159

PCT Pub. Date: Feb. 13, 1997

[30] Foreign Application Priority Data

Jul. 26, 1995 [CH] Switzerland .......................... 95810485

[51] Int. Cl.$^6$ .............................. C07K 17/00; A23J 1/00
[52] U.S. Cl. ......................... 530/413; 530/350; 530/351; 530/412; 530/415; 530/416; 530/417; 530/419; 530/420; 530/421; 530/427; 530/811; 530/812
[58] Field of Search .................................... 530/413, 350, 530/351, 412, 415, 416, 417, 419, 420, 421, 427, 811, 812

[56] References Cited

U.S. PATENT DOCUMENTS

| | | | |
|---|---|---|---|
| 5,136,025 | 8/1992 | Scheuermann et al. | 530/413 |
| 5,169,936 | 12/1992 | Staples et al. | 530/350 |

FOREIGN PATENT DOCUMENTS

| | | |
|---|---|---|
| 0051873 | 5/1982 | European Pat. Off. |
| 0205404 | 12/1986 | European Pat. Off. |
| 0253303 | 1/1988 | European Pat. Off. |

OTHER PUBLICATIONS

Heinemeyer et al., EMBO Journal, vol. 10, 1991, pp. 555–562.
Hinnen et al, "Yeast Genetic Engineering," Barr et al Eds., Butterworths, 1989, pp. 193–213.
Meister et al, J. Gen. Virol, vol. 67, 1986, pp. 1633–1643.
Hochkeppel et al., Drugs of the Future, vol. 17, 1992, pp. 899–914.
Sulkowski, Trends in Biotechnology, vol. 3, 1985, pp. 1–7.
Rassi & Horvath, J. Chromatography, vol. 359, 1986, pp. 241–253.
Figueroa et al., J. Chromatography, vol. 371, 1986, pp. 335–352.
Arnold, BIO/Technology, vol. 9, 1991, 151–156.
Wong et al., Separation and Purification Methods, vol. 20, 1991, pp. 49–106.
Porath, Protein Expression and Purfication, vol. 3, 1992, pp. 263–281.
Yip & Hutchens Methods in Molecular Biology, vol. 11, 1992, pp. 17–31.
Chadha et al., J. Gen. Virol., vol. 43, 1979 pp. 701–706.
Sulkowski et al., Affinity Chromatography and Related Techniques, 1982, pp. 313–322.
Hochuli, Chimia, vol. 40, 1986 pp. 408–412.
Hochuli, J. Chromatography, vol. 444 1988, pp. 293–302.
Zawistowska et al., Ceral Chem., vol. 65, 1988, pp. 413–416.
Vijayalakshim, TIBTECH, vol. 7, 1989, pp. 71–76.
Porath, Trends in Analytical Chem., vol. 7, 1988, pp. 254–259.
Yamashita et al, Proc. Natl. Acad. Sci. USA, vol. 87, 1990, pp. 5684–5652.
Yip et al., Analytical Biochem., vol. 183 pp. 159–171.
Hemdan & Porath, J. Chromatography, Vo, 323 1985, pp. 255–264.
Porath, Biotechnol. Progress, vol. 3, 1987, pp. 14–21.
Gregory et al., Protein Engineering, vol. 6, 1993, pp. 29–35.
Kagedal in Protein purification, principles, high resolution methods and applications; Janson and Ryden Eds., 1989, pp. 227–241.
Satchell & Satchell, Chemical Reviews, vol. 69, 1969, pp. 251–278.
Todd et al., Proteins, vol. 10, 1991, pp. 156–161.
Smith et al., Inorganic Chem., vol. 26, 1987, pp. 1965–1969.
Nakagawa et al., Analytical Biochem. vol. 168, pp. 75–81.
Nakagawa et al; *Analytical Biochemistry*, vol. 168, pp. 75–81, 1988.
Smith et al, *Inorg. Chem.*, vol. 26, pp. 1965–1969, 1987.
Alan G. Sharpe, *Inorganic Chemistry*, Published by Longman Group Limited London, Chapter 15, under 15.3, Hydrides, p. 377, 1981.
Baham et al, *Chemical Abstracts*, vol. 88, p. 636, Ref—#1891266 (J. Environ. Qual. 1978(2), pp. 181–188), 1978.
Sofer et al., *BioTechniques*, vol. 1, No. 4, pp. 198–203, 1983.
Bonnerjea et al *Bio/Technology*, vol. 4, pp. 955–958, 1986.

*Primary Examiner*—Cecilia J. Tsang
*Assistant Examiner*—Abdel A. Mohamed
*Attorney, Agent, or Firm*—Stephen G. Kalinchak; William K. Wissing

[57] ABSTRACT

The instant invention relate to a new method for the purification of proteins using copper chelate-affinity chromatography, wherein the impure or pre-purified protein is adsorbed on immobilized copper(II) ions, optionally washed with buffer and deionized water, washed with a solution of a Lewis-base, and finally eluted with deionized water.

23 Claims, No Drawings

METHOD FOR THE PURIFICATION OF PROTEINS

The instant invention relates to a new method for the purification of proteins using copper chelate-affinity chromatography.

Copper chelate-affinity chromatography functions by binding the accessible electron-donating group of a protein, such as histidine, to a copper ion which is held by a chelating group covalently attached on a stationary support. The presence of a single accessible histidine is usually sufficient for the adsorption of a protein on a copper(II)-IDA-chelate (IDA=iminodiacetate). Protein retention in copper chelate-affinity chromatography depends on the number and type of pendant groups on the protein which can interact with the metal. This interaction is affected by a variety of independent variables such as pH, temperature, solvent type, salt type and salt concentration. The proteins that are bound to the copper chelate in a neutral or low alkaline pH region are usually eluted by a decreasing pH gradient (continuous or stepwise) or by an increasing concentration gradient (continuous or stepwise) of a competitive agent, e.g. a Lewis-base such as imidazole, in a buffer. Alternatively, a third possible elution method includes a chelating agent, such as EDTA, in the eluent.

However these methods have several disadvantages:
- low selectivity, i.e. several proteins are eluted under the same conditions
- low enrichment
- co-elution of the protein with high concentrations of copper(II) ions if competitive or chelating agents are used
- further purification steps are necessary to remove the eluent
- usually a continuous gradient has to be applied for the elution of the desired protein, in order to increase the selectivity.

For example in case the protein is eluted using a competitive or a chelating agent the elution contains the protein, the competitive or chelating agent and released copper(II) ions. Therefore, the competitive agent and the copper(II) ions have to be removed by additional purification steps and, furthermore, a lot of proteins are unstable in presence of high concentrations of copper(II) ions in solution (oxidation) or at low pH values (precipitation) and are inactivated.

The current invention now provides a surprising advantageous method for the elution of proteins from a copper chelate-complex. Using the inventive method, it is surprisingly possible to elute the desired protein with deionized water that may optionally contain additional stabilizers for the protein. The use of deionized water has several advantages over the art:
- no competitive or chelating agent is used and therefore no additional purification steps are necessary
- the desired protein is not co-eluted with high concentrations of copper(II) ions that may cause oxidation problems
- the desired protein is not eluted at low pH values that may cause precipitation or inactivation problems
- the desired protein is recovered in a particularly high purity and with a high yield
- the elution can be carried out in one step instead of applying a gradient (continuous or stepwise)
- the eluted protein can be stored without further treatment.

DETAILED DESCRIPTION OF THE INVENTION

The current invention concerns a process for the enrichment of proteins comprising the steps:

a) adsorption of the impure or pre-purified protein on immobilized copper(II) ions, b) washing of the adsorbed protein with a solution of a Lewis-base, and c) eluting the desired protein with deionized water.

Usually the copper(II) ions are immobilized on a stationary support that is, e.g., an inorganic carrier such as silica or a polymeric matrix.

It is necessary that the stationary support is capable of forming chelats with copper(II) ions. Examples of such stationary supports are those in which chelating groups, such as imidoacetic acid (IDA), N,N,N'-tris(carboxymethyl)-ethylenediamine (TED), carboxymethylated aspartic acid (CM-ASP), tetraethylene pentamine (TEPA) nitriloacetic acid (NTA) or carboxymethylated α, β diamino succinic acid (CM-DASA), are covalently bound to the stationary support. The chelating groups may be attached to the stationary support directly or via spacers. The polymeric carrier may be any polymeric compound conventionally used for the metal ion-affinity-chromatography. Examples of such polymeric materials include agarose, dextrans or other synthetic polymers; preferred are agarose and vinyl polymers. Methods for the preparation of stationary supports having covalently attached chelating groups are described, for example, in Hochuli, CHIMIA (1986), 40, 408–412 (see also Figueroa et al., J. Chromatography (1986), 371, 335–352; Porath, Protein expression and purification (1992), 3, 263–281; L. Kågedal in "Protein purification, principles, high resolution methods and applications" Janson and Ryden Eds. (1989), 227–251, VCH Publishers, New York). In a preferred embodiment of the invention the stationary support is capable of forming chelats with copper(II) ions at a concentration of 1–200, and more preferably 10–100, μmol/ml of the stationary support.

Suitable polymeric carrier for use in the instant invention are also commercially available like:

CHELATING-SEPHAROSE FAST FLOW® (Pharmacia, Uppsala), in which iminodiacetic acid groups on spacers are coupled to Sepharose fast Flow by stable ether linkages;

CHELATING-SEPHAROSE 6B® (Pharmacia Uppsala) which also has iminodiacetic acid groups on spacers; and CHELATING TOYOPEARL-HELATE-650 M® (TosoHaas, Stuttgart), in which iminodiacetic acid groups are immobilized on a hydrophilic semirigid stationary support made of a copolymer from oligoethylene glycol, glycidyl methacrylate and pentaerythrol dimethacrylate.

Prior to the immobilization of copper(II) ions the stationary support is usually washed. For example, the stationary support is washed successively with 1–10, preferably 3–7, bed volumes of 5–50%, preferably 10–30%, ethanol; 1–10, preferably 3–7, bed volumes of deionized water; 1–10, preferably 3–7, bed volumes of 0.01–0.1 M, preferably 0.03–0.07 M, EDTA and 0.1–1 M, preferably 0.3–0.7 M, NaCl; 1–10, preferably 3–7, bed volumes of 0.05–1 M, preferably 0.1–0.5 M, NaOH and 0.1–5 M, preferably 0.5–2 M, NaCl; 1–15, preferably 3–10, bed volumes of deionized water; finally, 1–10, preferably 3–7, bed volumes of 0.01–1%, preferably 0.05–0.5%, formic acid and 1–15, preferably 3–10, bed volumes of deionized water. The flow rate of these washing solutions is usually 1–50, preferably 5–20, bed volumes per hour.

The immobilization of copper(II) ions in the above stationary support can be achieved simply by charging the stationary support with cupric ions. Common copper(II) ion sources are copper(II) salts, such as $CuCl_2$, $Cu(CH_3COO)_2$ and, especially, $CuSO_4$. Usually 1–10, preferably 3–7, bed volumes of a 0.001–0.1 M, preferably 0.003–0.01 M, aqueous $CuSO_4 \times 5\ H_2O$ solution are used and, subsequently, the stationary support is washed with a large excess of water in order to eliminate the remaining unbound cupric ions. The thus prepared stationary support containing immobilized copper(II) ions is ready for use for the process of the instant invention.

Depending on the stationary support, the pH and the ionic strength of the protein-containing solution it is sometimes preferred to treat the stationary support with a solution having the same pH and ionic strength prior to charging the protein-containing solution, to avoid swelling or shrinking when-adsorbing the protein. The necessity for such a treatment can readily be examined by a small scale test. This pre-treatment can be achieved by flowing 1–10, preferably 3–7, bed volumes of the treatment solution through the stationary support.

The adsorption of the protein to the above prepared stationary support through chelate formation is achieved simply by loading a solution containing the protein on the column containing the immobilized copper(II)-ions.

The protein solution may be of various origin and may be pre-purified or not. For example, if the protein to be isolated is secreted by the host into the culture broth it is, e.g., possible to apply the culture broth after centrifugation directly to the stationary support. If the protein is produced and stored within the host the cells have to be disrupted and the protein containing solution has to be separated from the cell debris, e.g. by centrifugation. The protein containing solutions obtained so far may be applied directly to the stationary support as described above or may be purified further, e.g., by precipitation, extraction or chromatographic means that are well known in the art. Accordingly, the solution containing the protein may be of various origin, and it may contain various impurities, such as ionic species, foreign proteins etc.

Whether a protein may be purified with the inventive method or not can be determined easily in a small scale test wherein the protein is adsorbed to a small amount of the copper(II) charged stationary support, treated with a Lewis-base as defined below and subsequently the amount of protein that can be eluted with deionized water is determined and compared to the amount of protein that can be eluted with 2M $NH_4Cl$. In general the inventive process may be applied to proteins characterized in that a Lewis-base as defined below does not destroy totally a complex between said protein and copper(II) ions. Preferred proteins are interferon, amylase, trypsin and related proteins. Especially preferred are interferon-$\alpha$, trypsin and $\alpha$-amylase.

The amount of the protein-containing solution to be loaded on the stationary support is dependent on the copper (II) ion concentration immobilized on this stationary support, the concentration of the protein in the solution and the nature of the protein. Therefore, the proper amount of solution to be loaded is determined empirically by observing the effluent using a detector, such as a UV monitor.

An important step according to the invention is the washing of the protein adsorbed to the stationary support with a Lewis-base prior to the elution with deionized water. A Lewis-base is an electron-pair donor like amins, $HO^-$, phosphane or phosphines. Examples are, $NH_3$, $CH_3NH_2$, $(CH_3)_2NH$, $(CH_3)_3N$, $C_2H_5(CH_2)_2N$, $C_2H_5NH_2$, $(C_2H_5)_2NH$, $(C_2H_5)_3N$, $C_3H_7NH_2$, $C_4H_9NH_2$, $C_5H_{11}NH_2$, $C_6H_{13}NH_2$, $CH_3PH_2$, $(CH_3)_2PH$, $(CH_3)_3P$, amino acids, cystine, amines carrying hydroxyl groups like $HOCH_2NH_2$, $(HOCH_2)_2NH$ or $(HOCH_2)_3N$, $HOC_2H_4NH_2$, $(HOC_2H_4)_2NH$ or $(HOC_2H_4)_3N$; or TRIS-HCl.

In a preferred form of the invention the Lewis-base solution contains $NH_4^+$ or a primary, secondary or ternary amine in a neutral or low alkaline pH region or $OH^-$ at a high alkaline pH region. In a more preferred embodiment of the invention the Lewis-base solution contains $NH_4^+$ or a primary, secondary or ternary amine and most preferred is a solution containing $NH_4^+$ or a primary amine like ethanolamine, cystine, $NH_4SCN$, $NH_4Cl$, $NH_4^+CH_3COO^-$, $(NH_4)_2SO_4$ and TRIS-HCl.

In order not to elute the desired protein with the Lewis-base solution the concentration of the Lewis-base or the pH of the solution containing the Lewis-base can be regulated. A preferred range for the concentration of the amine (Lewis-base) is from 0.001 to 1 M.

The optimal concentration of the Lewis-base strongly depends on the electron donor. For example, a concentration of 1 mM is optimal in the case of cystine, whereas the concentration of 300–500 mM is optimal in the case of $NH_4Cl$. Optimal concentrations of several salts are, e.g., 10–100 mM for $NH_4SCN$, 10–500 mM for $NH_4Cl$, 10–800 mM or more for $NH_4(CH_3COO)$ and 10–500 mM or more for $(NH_4)_2SO_4$.

In case an amine is used as the Lewis-base, the pH is adjusted, preferably, to pH 6–9; more preferably 6.5–8.5; and most preferably 7.0–8.0. In case $OH^-$ is used as Lewis-base the pH is adjusted preferably to 9–11 for example with borate or phosphate buffer.

It is also possible to use mixtures of different Lewis-bases to improve the results or to add additional salts that are no Lewis-bases like NaCl or KCl. The concentration of the additional salt(s) may be up to 5M and preferably up to 2M.

Typically the stationary support to which the protein is already adsorbed is washed with 1–10 or, preferably, 3–7 bed volumes of the washing solution described above. The flow rate is determined empirically and is, for example, 1–10 or, preferably, 3–5 bed volume/hour.

The washing step as described above is advantageously accomplished just before the elution of the protein with deionized water. It is also possible to carry out this washing step simultaneously with the loading of the protein, provided that the elution step follows immediately thereafter.

The desired protein can be eluted after the washing with Lewis-base as described above by simply washing the stationary support with deionized water. For obtaining a high purity the deionized water should not contain more than 0.001 M ionic compounds. In contrast thereto, the deionized water may contain non-ionic compounds, e.g., to stabilize the ternary or quaternary structure of the protein. Suitable non-ionic compounds are, for example, sugar or polyols like mannitol, glucose, lactose, fructose, glycerol, polyethyleneglycol; or other compounds that maintain the oxidation state of the sulfhydryl-groups of the protein. The deionized water is preferably used in an amount of 1–10 and more preferably 3–7, bed volumes.

In the process of the instant invention, most foreign proteins that are specifically bound to the stationary support do not elute with deionized water. They stay adsorbed and can be removed afterwards using a classical elution solution (e.g. 2 M $NH_4Cl$ in 25 mM TRIS-HCl buffer pH 7.6). Therefore, the resulting enrichment of the product is especially high. For example, for the case of interferon-$\alpha$ $B_1D_2B_3B_4$, the product purity is as high as about 90%, starting from an adsorption solution of 30% purity, whilst the prior art copper chelate-affinity-chromatography achieves a purity of only 30–50%.

To optimize the purity and recovery of the desired protein one or more additional washing steps with an appropriate buffer, such as potassium borate buffer and/or with deionized water, may optionally be inserted between the protein adsorption step and the washing step with Lewis-base. Accordingly, in a more preferred embodiment of the invention the adsorbed protein is washed with a buffer that is not a Lewis-base, and/or with deionized water prior to washing with a solution of a Lewis-Base. This finding is surprising as the wash step and the elution step can be carried out using the same mean, namely deionized water.

This intermediate washing step using deionized water is effective, e.g., for eliminating side products, especially those bound to the stationary support through hydrophobic interactions (and not through specific copper ion affinity).

As known from other purification procedures based on copper(II) chelats, the solution of the isolated protein may contain minor amounts of copper(II) ions. These ions can be removed easily by methods known in the art like ion exchange or copper(II) ion chelating columns. The latter purification step may be carried out separately or immediately afterwards, for example by filling the lower part of the column with the copper(II) ion removing material.

After the purification the copper charged stationary support may be washed and used for another purification or, preferably to obtain reproducible results, the copper(II) ions are removed from the stationary support with a competitive chelating agent, e.g. EDTA and, subsequently, the stationary support is charged again with copper(II) ions as described above.

EXAMPLES

Example 1

Purification of IFN-B/D

The recombinant human hybrid interferon-$\alpha$ $B_1D_2B_3B_4$, which is referred to hereinafter as IFN-B/D, is, constructed as described in EP-A-205404. IFN-B/D is produced by *Saccharomyces cerevisiae* strain HT 393, which is identical to E 95-1-2A published by Heinemeyer et al. (EMBO Journal (1991), 10, 555–562; DSM 9697) and which has been transformed with plasmid pDP34R/PHO5/IFN AM119. The yeast vector pDP34R and the yeast acid phosphatase gene promoter PHO5 refer to Hinnen et al. (in: "Yeast Genetic Engineering", Barr et al. Eds, Butterworths, Boston, (1989), 193–213). IFN AM119 is the coding sequence of IFN-B/D and refers to EP-A-205404.

The yeast strain HT 393 containing the recombinant plasmid coding for IFN-B/D is grown in large fermentation tanks. After the fermentation is completed, the biomass is collected by centrifugation. The cell sediment obtained is diluted to a wet cell concentration of 50% (dry cell concentration about 10%) with a 0.07 M potassium phosphate buffer pH 7 containing 0.5 M NaCl. After cell disruption by passage through a glass-bead mill, the IFN-B/D protein is extracted from the cell homogenate by partitioning in an aqueous two-phase system containing 40% by weight of the cell homogenate, 18% by weight of polyethylene glycol 1500, 4% by weight of potassium phosphate pH 7 and NaCl at a total concentration of 1 mol/kg. After phase separation by passage through a centrifugal disk stack separator at 8150 rpm (13000 g), the top phase is collected and washed by partitioning in a second aqueous two-phase system formed by mixing 4 parts by weight of the top phase and 1 part by weight of a 1 mol/kg NaCl solution containing 20% by weight of potassium phosphate pH 7. After phase separation in a settling tank, IFN-B/D is recovered from the new top phase obtained by back extraction in a third aqueous two-phase system generated by mixing 3 parts by weight of the top phase of the second two-phase system and 7 parts by weight of a 1.56 mol/kg magnesium sulfate solution. After phase separation in a settling tank, the heavy phase is collected, diluted with a double volume of water, filtered through a 0.2 micron filter, then stored at 4° C. for a few days before processing by copper chelate chromatography.

This adsorption solution has the following characteristics: pH 5.6, conductivity about 43 mS/cm (mainly due to $MgSO_4$), polyethylene glycol concentration 6 mg/ml, IFN-B/D concentration of about 0.1–0.15 mg/ml, IFN-B/D purity of about 30% of the total protein content.

The copper chelate chromatography is performed at room temperature, using a column (diameter 44 mm) filled with 100 ml of CHELATING-SEPHAROSE FAST FLOW® (Pharmacia, Uppsala). The stationary support is washed successively with: 5 bed volumes of 20% ethanol, 5 bed volumes of deionized water, 5 bed volumes of 0.05 M EDTA and 0.5 M NaCl, 5 bed volumes of 0.25 M NaOH and 1 M NaCl, 7 bed volumes of deionized water, 5 bed volumes of 0.1% formic acid and 7 bed volumes of deionized water, at a flow rate of 12 bed volumes per hour. Then the stationary support is charged with cupric ions by loading 5 bed volumes of a 0.008 M $CuSO_4$-5 $H_2O$ solution and rinsed with large amounts of deionized water, in order to eliminate the remaining unbound copper. Before the adsorption step, the column is equilibrated with 500 ml of a buffer solution composed of 0.68 M $MgSO_4$ and 0.092 M sodium acetate pH adjusted to 5.6 with acetic acid, having about the same conductivity as the adsorption solution, i.e. 43 mS/cm. Then a volume of 5000 ml of the IFN-B/D adsorption solution is loaded on the column at a flow rate of 300 ml/h. The effluent is followed by a UV-monitor set at the wavelength of 280 nm.

After loading, three successive washings are carried out at a flow rate of 500 ml/h: the first one with 500 ml of the equilibration buffer pH 5.6 already used before the adsorption, the second one with 500 ml of deionized water and the third one with 500 ml of 0.025 M TRIS-HCl buffer pH 7.6 containing 0.2 M $NH_4Cl$ and 1 M NaCl. Then IFN-B/D is eluted by using simply again 400 ml of deionized water at the flow rate of 500 ml/h. The three washes and the water eluate are collected as controlled by the UV-monitor.

The IFN-B/D concentration of the adsorption solution, of the three washes and of the water eluate is measured by reverse phase HPLC analysis (column: Vydac C-18, 30 nm, particle size 5 micron; mobile phase A: 0.1% trifluoroacetic acid in water, mobile phase B: 80% acetonitrile, 19.91% water and 0.09% trifluoroacetic acid; flow rate 1 ml/min; injection volume 0.05 ml; UV-detection at 216 nm).

The amount of IFN-B/D found in the three washes is negligible. Contrary to all expectations, the water eluate is found to contain IFN-B/D recovered with a yield of about 70% and having a high purity: about 90% of the total protein content (i.e. enrichment of IFN-B/D by a factor 3).

This water elution is particularly surprising, as no IFN-B/D is found in the second wash (recovery yield smaller than 5%), which consists exactly of the same liquid, that is pure water.

The water eluate, which has a particularly high IFN-B/D concentration (about 1 mg/ml) at low salt concentration and at a pH value of about 8, is stable when stored at 4° C.: no precipitation of IFN-B/D occurs over days.

Example 2

Characterization of Various IFN-B/D Solutions Obtained by Water Elution

Aqueous solutions of IFN-B/D are obtained by water elution in a similar way as described in example 1, but changing the volume of water used for the elution and/or the composition of the buffer used for the washing step just preceding the water elution.

A first IFN-B/D solution is obtained by using the same washing buffer as mentioned in example 1 (0.025 M TRIS-HCl buffer pH 7.6 containing 0.2 M $NH_4Cl$ and 1 M NaCl) and using only about 0.67 bed volume of deionized water for the elution.

A second IFN-B/D solution is obtained by using 0.025 M potassium phosphate buffer pH 7.6 containing 0.2 M $NH_4Cl$ as washing buffer and 1.5 bed volume of deionized water for the elution.

A third IFN-B/D solution is obtained by using 0.025 M TRIS-HCl buffer pH 7.6 (without $NH_4Cl$ and without NaCl) as washing buffer and 4 bed volumes of deionized water for the elution. The characteristics of the three IFN-B/D solutions are given in Table 1.

TABLE 1 characteristics of various IFN-B/D solutions obtained by water elution

| washing buffer used | concentration of IFN-B/D (mg/ml) | pH | conductivity (mS/cm) |
|---|---|---|---|
| 0.025M TRIS-HCl pH 7.6 + 0.2M $NH_4Cl$ + 1.0M NaCl | 7.0 | 8.8 | 11.3 |
| 0.025M K-phosphate pH 7.6 + 0.2M $NH_4Cl$ | 2.5 | 7.6 | 7.4 |
| 0.025M TRIS-HCl pH 7.6 | 1.5 | 8.2 | 0.4 |

The first solution has a particularly high interferon concentration (7 mg/ml) and is found to be surprisingly stable when stored at 4° C.: no precipitation of IFN-B/D occurs over night. In comparison, the solubility of pure IFN-B/D in 0.1 M potassium phosphate buffer pH 7.6 or in 0.1 M sodium bicarbonate buffer pH 8.0 is lower than 0.5 mg/ml.

The second and the third solutions are stored over days at 4° C. For both of these solutions, the interferon concentration measured by reverse phase HPLC analysis (as described in example 1) is found to be unchanged after 1 week. This stability is particularly surprising in the case of the third solution, which has a very low salt concentration (conductivity<0.5 mS/cm) at an interferon concentration as high as 1.5 mg/ml.

Example 3

Estimation of the Recovery Yields for the Elution of IFN-B/D

The experiments are performed at room temperature, using a FPLC® chromatography system (Pharmacia, Uppsala) and a glass column (diameter 10 mm) filled with 5 ml of CHELATING-SEPHAROSE FAST FLOW® (Pharmacia, Uppsala). The flow rate is set at 60 ml/h for all the solutions pumped through the column. The effluent is followed by a UV-monitor set at the wavelength of 280 nm. The regeneration and the preparation of the stationary support are carried out as described in example 1, by pumping successively the following solutions through the column: 25 ml of 0.05 M EDTA and 0.5 M NaCl, 25 ml of 0.25 M NaOH and 1 M NaCl, 35 ml of deionized water, 25 ml of 0.1% formic acid, 35 ml of deionized water, 25 ml of 0.008 M $CuSO_4 \times 5$ $H_2O$ and 40 ml of deionized water.

In a first experiment, about 80 ml of a solution of pure IFN-B/D (purity: 99.9% of the protein content; concentration: about 0.3 mg/ml) in 0.2 M mannitol and 0.03 M sodium phosphate pH 7.6 is loaded on the column. After washing with 35 ml of 0.3 M ammonium chloride buffer pH 7.6, the interferon is eluted by using 35 ml of deionized water. Then, a volume of 35 ml of 0.025 M TRIS-HCl buffer pH 7.6 containing 2M ammonium chloride is pumped through the column in order to ensure the elution of all the interferon still bound on the stationary support. The interferon concentration of the fractions collected is measured by reverse phase HPLC analysis as described in example 1. The corresponding recovery yields obtained are given in Table 2.

The same experiment is repeated, but using 0.1 M potassium borate pH 7.6 as washing buffer instead of 0.3 M ammonium chloride pH 7.6. The results are also given in Table 2.

TABLE 2 recovery yields for the elution of IFN-B/D

| washing buffer used | % eluted with washing buffer | % eluted with $H_2O$ | % eluted with 2M $NH_4Cl$ |
|---|---|---|---|
| 0.3M $NH_4Cl$ pH 7.6 | 0 | 92 | 8 |
| 0.1M K-borate pH 7.6 | 0 | 9 | 91 |

As shown in Table 2, the composition of the buffer used for the washing step just preceding the elution affects largely the elution with water.

Example 4

Influence of the Washing Step

The same experiment as stated in example 3 is carried out several times, changing only the composition of the washing buffer. The various washing buffers tested and the corresponding recovery yields obtained are listed in Table 3.

TABLE 3 recovery yields for the elution of IFN-B/D

| washing buffer used | % eluted with washing buffer | % eluted with $H_2O$ | % eluted with 2M $NH_4Cl$ |
|---|---|---|---|
| 0.1M K-borate pH 7.6 | 0 | 9 | 91 |
| 0.1M K-borate pH 8.5 | 0 | 35 | 65 |
| 0.1M K-borate pH 9.5 | 0 | 66 | 34 |
| 0.3M K-acetate pH 7.6 | 0 | 26 | 74 |
| 0.3M $NH_4$-acetate pH 7.6 | 0 | 85 | 15 |
| 0.2M $N(CH_3)_4Cl$ pH 7.6 | 0 | 12 | 88 |
| 0.2M triethanolamine pH 7.6 | 0 | 68 | 32 |
| 0.2M diethanolamine pH 7.6 | 0 | 70 | 30 |
| 0.2M ethanolamine pH 7.6 | 0 | 82 | 18 |
| 0.3M $NH_4Cl$ pH 7.6 | 0 | 92 | 8 |
| 0.001M cystine pH 7.6 | 0 | 77 | 23 |
| 0.5M $NH_4Cl$ pH 7.6 | 19 | 72 | 9 |

As shown in Table 3, the elution with water occurs with a good yield (higher than 60%) either if the washing buffer has a pH value in the basic range (e.g. with 0.1 M potassium borate pH 9.5), or if the washing buffer contains an amine or an ammonium salt at a nearly neutral pH value (e.g. with 0.3 M ammonium acetate pH 7.6, but not with 0.3 M potassium acetate pH 7.6). In this case, the amine is allowed to be primary (e.g. ethanolamine), secondary (e.g. diethanolamine) or tertiary (e.g. triethanolamine), but not quaternary (e.g. tetramethylammonium chloride). The optimal concentration of the washing buffer depends largely upon the amine used: for example about 1 mM in the case of cystine pH 7.6 or 300–500 mM in the case of NH$_4$Cl pH 7.6.

Example 5

Influence of a Second Washing Step After the Lewis-Base Treatment

The same experiment as stated in example 3 is repeated, but inserting a second washing step with 35 ml of 0.1 M potassium borate buffer pH 7.6 between the first washing step done with 35 ml of 0.3 M ammonium chloride buffer pH 7.6 and the elution with water. The recovery yields found are:

| | | |
|---|---|---|
| in the first wash | (0.3M NH$_4$Cl pH 7.6): | 0% |
| in the second wash | (0.1M K-borate pH 7.6): | 0% |
| in the first eluate | (water): | 22% |
| in the second eluate | (2M NH$_4$Cl + 0.025M TRIS-HCl pH 7.6): | 78%. |

A small amount of IFN-B/D is found in the water eluate. But in spite of the presence of ammonium in the first washing step, the recovery yield obtained is low (about 22%), indicating a higher influence of the washing step just preceding the elution.

Example 6

Recovery Yields for the Elution of IFN-B/D Without Washing Step

The same experiment as stated in example 3 is repeated, but without washing step between the adsorption step and the elution step with water.

A first run is carried out using exactly the same loading solution as mentioned in example 3 (0.3 mg/ml IFN-B/D in 0.2 M mannitol and 0.03 M sodium phosphate pH 7.6). A second run is then carried out also with the same loading solution, but containing additionally ammonium chloride at a concentration of 0.3 Mol/l. The corresponding recovery yields obtained are given in Table 4.

TABLE 4 recovery yields for the elution of IFN-B/D (case without washing step)

| loading buffer | % eluted with H$_2$O | % eluted with 2M NH$_4$Cl |
|---|---|---|
| 0.03M Na-phosphate pH 7.6 + 0.2M mannitol | 37 | 63 |
| 0.03M Na-phosphate pH 7.6 + 0.2M mannitol + 0.3M NH$_4$Cl | 95 | 5 |

As shown in Table 4, the composition of the loading buffer just preceding the elution affects largely the elution with water.

Example 7

Influence of the Salting-Out Effect

An aqueous solution of partially pure IFN-B/D (purity: about 90% of the protein content) is obtained by water elution in a similar way as described in example 1. Aliquots of this solution are frozen, stored at about −5 to −10° C. and thawed before use.

The composition of this stock solution is:

| | |
|---|---|
| IFN-B/D: | 0.5–1 mg/ml |
| TRIS-HCl: | about 0.02M |
| NaCl: | about 0.01M |
| Na-acetate: | about 0.01M |
| NH$_4$Cl: | about 0.002M |
| Cu$^{2+}$: | about 1 µM |
| pH: | 8 |
| conductivity: | 2.2 mS/cm |

The same experiment as stated in example 3 is carried out several times, loading 50 ml of this stock solution and changing only the composition of the washing buffer. The various washing buffers tested and the corresponding recovery yields obtained are listed in Table 5.

TABLE 5 recovery yields for the elution of IFN-B/D

| washing buffer used | % eluted with washing | % eluted with H$_2$O | % eluted with 2M NH$_4$Cl |
|---|---|---|---|
| 0.025M NH$_4$SCN pH 7.6 | 0 | 84 | 16 |
| 0.1M NH$_4$SCN pH 7.6 | 0 | 96 | 4 |
| 0.2M NH$_4$SCN pH 7.6 | 50 | 50 | 0 |
| 0.3M NH$_4$SCN pH 7.6 | 98 | 2 | 0 |
| 0.4M NH$_4$SCN pH 7.6 | 100 | 0 | 0 |
| 0.5M NH$_4$SCN pH 7.6 | 100 | 0 | 0 |
| 0.025M NH$_4$Cl pH 7.6 | 2 | 97 | 1 |
| 0.1M NH$_4$Cl pH 7.6 | 0 | 100 | 0 |
| 0.2M NH$_4$Cl pH 7.6 | 0 | 100 | 0 |
| 0.3M NH$_4$Cl pH 7.6 | 0 | 96 | 4 |
| 0.5M NH$_4$Cl pH 7.6 | 8 | 91 | 1 |
| 0.8M NH$_4$Cl pH 7.6 | 19 | 81 | 0 |
| 0.025M NH$_4$-acetate pH 7.6 | 0 | 89 | 11 |
| 0.1M NH$_4$-acetate pH 7.6 | 0 | 97 | 3 |
| 0.5M NH$_4$-acetate pH 7.6 | 0 | 98 | 2 |
| 0.8M NH$_4$-acetate pH 7.6 | 0 | 100 | 0 |
| 0.025M (NH$_4$)$_2$SO$_4$ pH 7.6 | 0 | 80 | 20 |
| 0.1M (NH$_4$)$_2$SO$_4$ pH 7.6 | 0 | 98 | 2 |
| 0.2M (NH$_4$)$_2$SO$_4$ pH 7.6 | 0 | 96 | 4 |
| 0.3M (NH$_4$)$_2$SO$_4$ pH 7.6 | 0 | 100 | 0 |
| 0.5M (NH$_4$)$_2$SO$_4$ pH 7.6 | 0 | 97 | 3 |

All the washing buffers tested are ammonium salts at pH 7.6. The anions used as counter-ions are arranged in Table 5 in order from those that show a tendency to disrupt the structure of water (chaotropic effect) and lead to a relative decrease in the strengths of hydrophobic interactions to those that are particularly effective in increasing hydrophobic interactions (salting-out effect):

increasing salting-out effect: $SCN^- < Cl^- < CH_3COO^- < SO_4^{2-}$

As shown in Table 5:

In the case of NH$_4$SCN (low salting-out effect), if the ammonium concentration is too high ($\geq$0.3 M), IFN-B/D is directly eluted with the washing buffer. The water elution occurs with a high yield ($\geq$90%) when the concentration of NH$_4$SCN is$\leq$0.1 M.

In the case of NH$_4$Cl, the water elution occurs with a high yield when the concentration of NH$_4$Cl is$\leq$0.5 M.

In the case of NH$_4$-acetate, it is possible to use a concentration as high as 0.8 M and to obtain a high yield for the water elution.

In the case of (NH$_4$)$_2$SO$_4$ (high salting-out effect), it is possible to use an ammonium concentration as high as 1.0 M and to obtain a high yield for the water elution.

Example 8

Influence of pH and Concentration

Same experiments as stated in example 7 are repeated, changing the composition of the washing buffer. The various washing buffers tested and the corresponding recovery yields obtained are listed in Table 6.

TABLE 6 recovery yields for the elution of IFN-B/D

| washing buffer used | % eluted with washing buffer | % eluted with $H_2O$ | % eluted with 2M $NH_4Cl$ |
|---|---|---|---|
| 0.025M K-acetate pH 5.6 | 0 | 5 | 95 |
| 0.1M K-acetate pH 5.6 | 0 | 9 | 91 |
| 0.25M K-acetate pH 5.6 | 0 | 6 | 94 |
| 0.5 K-acetate pH 5.6 | 0 | 3 | 97 |
| 0.025M TRIS-HCl pH 5.6 | 0 | 21 | 79 |
| 0.1M TRIS-HCl pH. 5.6 | 0 | 21 | 79 |
| 0.3M TRIS-HCl pH 5.6 | 0 | 22 | 78 |
| 0.5M TRIS-HCl pH 5.6 | 0 | 17 | 83 |
| 0.025M TRIS-HCl pH 7.6 | 0 | 62 | 38 |
| 0.1M TRIS-HCl pH 7.6 | 0 | 89 | 11 |
| 0.3M TRIS-HCl pH 7.6 | 1 | 89 | 10 |
| 0.5M TRIS-HCl pH 7.6 | 26 | 71 | 3 |
| 0.025M TRIS-HCl pH 7.6 + 1.7M NaCl | 0 | 98 | 2 |
| 0.1M TRIS-HCl pH 7.6 + 1.7M NaCl | 0 | 98 | 2 |
| 0.2M TRIS-HCl pH 7.6 + 1.7M NaCl | 10 | 89 | 1 |

As shown in Table 6:

In the case of K-acetate pH 5.6 (low pH value; no amine) and in the case of TRIS-HCl pH 5.6 (low pH value; presence of amine), the recovery yields obtained for the water elution are very low.

In the case of TRIS-HCl pH 7.6 (nearly neutral pH value; presence of amine), the recovery yield obtained for the water elution is good (higher than 60%). If the amine concentration is too high (>0.3 M), a partial elution of IFN-B/D occurs directly with the washing buffer. If the amine concentration is too low (<0.1 M), the water elution is not quantitative and a remaining amount of IFN-B/D can be eluted afterwards by using the 2 M $NH_4Cl$+0.025 M TRIS-HCl buffer pH 7.6. This last problem can be avoided by the inclusion of NaCl (at a concentration of 1.7 M), which will quench ionic interactions between the stationary support and the interferon protein.

Example 9

Elution With a Gradient

The same experiment as stated in example 7 is carried out, using 0.1 M TRIS-HCl pH 7.6 as washing buffer. The recovery yield obtained for the water elution is 89%. The remaining amount of IFN-B/D (11%) is eluted afterwards with the 2 M $NH_4Cl$+0.025 M TRIS-HCl buffer pH 7.6.

This experiment is repeated using the same washing buffer (20 ml 0.1 M TRIS-HCl pH 7.6), but after this washing step a linear gradient elution is carried out from 100% washing buffer to 100% deionized water in 12 bed volumes (60 ml). The column is rinsed further with 55 ml of water and then a second linear gradient is applied from 100% water to 100% of the 2 M $NH_4Cl$+0.025 M TRIS-HCl buffer pH 7.6 in 7 bed volumes (35 ml). The column is finally rinsed with 15 ml of this last buffer.

IFN-B/D is found to be eluted at the end of the first gradient, at a corresponding concentration of about 10 to 5 mM TRIS-HCl pH 7.6 and with a recovery yield of 60%. The remaining amount of IFN-B/D (40%) is eluted at the middle of the second gradient, at a corresponding concentration of about 1 M $NH_4Cl$+12.5 mM TRIS-HCl pH 7.6.

Example 10

Composition of the Elution Solution

Same experiments as stated in example 7 are repeated, using always a solution of 0.1 M TRIS-HCl pH 7.6 as washing buffer, but changing the composition of the first elution solution, namely the composition of the water for elution. The various elution solutions tested and the corresponding recovery yields obtained are listed in Table 7.

TABLE 7 recovery yields for the elution of IFN-B/D

| elution solution | conductivity (mS/cm) | % eluted with washing buffer | % eluted with elution solution | % eluted with 2M $NH_4Cl$ |
|---|---|---|---|---|
| $H_2O$ (deionized) | 0.0012 | 0 | 89 | 11 |
| 0.001M NaCl | 0.17 | 0 | 45 | 55 |
| 0.003M NaCl | 0.36 | 0 | 18 | 82 |
| 0.005M NaCl | 0.59 | 0 | 2 | 98 |
| 0.001M MES | ≦0.03 | 0 | 59 | 41 |
| 0.010M MES | ≦0.03 | 0 | 0 | 100 |
| 0.002M mannitol | ≦0.03 | 0 | 87 | 13 |
| 0.010M mannitol | ≦0.03 | 0 | 77 | 23 |
| 0.5M mannitol | ≦0.03 | 0 | 90 | 10 |
| 2.7M glycerol | ≦0.03 | 0 | 65 | 35 |

As shown in Table 7:

The residual salt concentration in water has to be extremely low (<0.001 M) in order to get an elution of IFN-B/D with a recovery yield higher than 50%.

Uncharged solutes as mannitol or glycerol are allowed to be present in the elution solution, even at high concentration (in the range of 1 M), but zwitterions are not. For example, the concentration of MES (2-[N-Morpholino]ethanesulfonic acid) has to be lower than 0.001 M in order to get a good recovery yield.

The conductivity of the elution solution cannot be used as a criterion in order to predict the occurrence or the non-occurrence of the elution of IFN-B/D.

Example 11

IFN-B and IFN-D

The experiments are performed with human interferon-α B (IFN-B) or with human interferon-α D (IFN-D) as described in example 3 for human hybrid interferon-α $B_1D_2B_3B_4$ (IFN-B/D), but using a smaller glass column (diameter 5 mm) filled with only 0.5 ml of Chelating-Sepharose Fast Flow® (Pharmacia, Uppsala). The corresponding flow rate and the corresponding volumes of the solutions pumped through the column are scaled down by a factor 10.

IFN-B and IFN-D, the parent molecules of IFN-B/D described in EP-A-205404, are produced by expression of recombinant DNA in yeast (*Saccharomyces cerevisiae*), fermentation, recovery and partial purification.

For IFN-B, a stock solution is obtained in 0.025 M TRIS-HCl buffer pH 7.6, which has an interferon concentration of 0.05 mg/ml and about the same purity as the IFN-B/D stock solution described in example 7.

For IFN-D, a stock solution is obtained, which has the same composition and about the same purity as the IFN-B/D adsorption solution described in example 1.

As described in example 3, the interferon loaded on the column is successively washed with an appropriate buffer, eluted with deionized water and eluted with 0.025 M TRIS-HCl buffer pH 7.6 containing 2 M ammonium chloride. The interferon concentration of the fractions collected is measured by reverse phase HPLC analysis as described in example 1, and confirmed by analysis of the biological antiviral activity on bovine cells (Madin-Darby bovine cells) against vesicular stomatitis virus in vitro. The various washing buffers tested and the corresponding recovery yields obtained are listed in Table 8.

TABLE 8 recovery yields for the elution of IFN-B or IFN-D

| IFN | washing buffer used | % eluted with washing buffer | % eluted with $H_2O$ | % eluted with 2M $NH_4Cl$ |
|---|---|---|---|---|
| IFN-B | 0.1M TRIS-HCl pH 7.6 | 0 | 53 | 47 |
| " | 0.3M TRIS-HCl pH 7.6 | 39 | 61 | 0 |
| " | 0.3M $(NH_4)_2SO_4$ pH 7.6 | 18 | 82 | 0 |
| " | 0.3M $NH_4$-acetate pH 7.6 | 2 | 98 | 0 |
| IFN-D | 0.01M TRIS-HCl pH 7.6 | 0 | 91 | 9 |

As shown in Table 8, IFN-B and IFN-D can be eluted with water.

Example 12

α-Amylase and Trypsin

The experiments are performed with various proteins as described in example 3 for IFN-B/D, using the same FPLC® chromatography system, the same amount (5 ml) of CHELATING-SEPHAROSE FAST FLOW® and the same chromatography conditions.

The proteins tested are: α-amylase from *Bacillus species* (Sigma product N° A 6380), trypsin from bovine pancreas (Serva product N° 37260). The runs are carried out by loading about 50 ml of the corresponding protein solution (concentration 0.5 mg/ml), either in 0.01 M TRIS-HCl buffer pH 7.6 if TRIS-HCl is used as following washing buffer, or in 0.01 M potassium borate buffer pH 7.6 if K-borate is used as following washing buffer or if the washing step is omitted.

As described in example 3, the protein loaded on the column is successively washed with a buffer (TRIS-HCl or K-borate), eluted with deionized water and eluted with 0.025 M TRIS-HCl buffer pH 7.6 containing 2 M ammonium chloride. The protein concentration of the fractions collected is measured by the Bio-Rad protein assay (Bio-Rad product N° 500-0006, microassay procedure). The proteins and the washing buffers tested, as well as the corresponding recovery yields obtained, are listed in Table 9.

TABLE 9

| protein | washing buffer used | % eluted with washing buffer | % eluted with $H_2O$ | % eluted with 2M $NH_4Cl$ |
|---|---|---|---|---|
| α-amylase | 0.010M TRIS-HCl pH 7.6 | 0 | 71 | 9 |
| " | 0.025M TRIS-HCl pH 7.6 | 0 | 97 | 3 |
| " | 0.050M TRIS-HCl pH 7.6 | 0 | 97 | 3 |
| " | 0.100M TRIS-HCl pH 7.6 | 5 | 89 | 6 |
| " | 0.300M TRIS-HCl pH 7.6 | 100 | 0 | 0 |
| " | 0.100M K-borate pH 7.6 | 0 | 15 | 85 |
| " | 0.100M K-borate pH 9.5 | 0 | 100 | 0 |
| " | no washing buffer | — | 22 | 78 |
| trypsin | 0.025M TRIS-HCl pH 7.6 | 0 | 43 | 57 |

As shown in Table 9:

α-Amylase (from *Bacillus species*) can be eluted with water (recovery yield: about 90–100%), either if the washing buffer has a pH value in the basic range (for example with 0.1 M potassium borate pH 9.5), or if the washing buffer contains an amine at a nearly neutral pH value and at an adequate concentration (for example with 0.025 to 0.1 M TRIS-HCl pH 7.6).

Trypsin (from bovine pancreas) can also be eluted with water (recovery yield higher than 40%), for example by using 0.025 M TRIS-HCl pH 7.6 as washing buffer.

Example 13

Chromatographic Media

The same experiment as stated in example 7 is carried out twice, using always 0.1 M TRIS-HCl pH 7.6 as washing buffer, but changing the chromatography medium.

For the first run, the medium used is Chelating-Sepharose Fast Flow® (Pharmacia, Uppsala), as in examples 1 to 12. The bead diameter is 0.045–0.165 mm. Chelating-Sepharose Fast Flow consists of iminodiacetic acid groups on spacers, coupled to Sepharose Fast Flow® by stable ether linkages:

[Sepharose Fast Flow]—O—$CH_2$—CHOH—$CH_2$—O—$CH_2$—CHOH—$CH_2$—N—$(CH_2COOH)_2$ The base matrix—Sepharose Fast Flow—is cross-linked agarose.

For the second run, the medium used is TSK Toyopearl® AF-Chelate-650 M (TosoHaas, Stuttgart). The bead diameter is about 0.065 mm. TSK Toyopearl® is a hydrophilic semi-rigid gel, a copolymer of oligoethyleneglycol, glycidylmethacrylate and pentaerythroldimethacrylate. The ligand consists of immobilized iminodiacetic acid groups.

For each run, a glass column (diameter 10 mm) is filled with 5 ml of the respective gel. The same method of regeneration and preparation (loading of the cupric ions) is applied for the Chelating-Sepharose Fast Flow® medium and for the TSK Toyopearl AF-Chelate-650 M® medium, as described in example 3. The adsorption solution of IFN-B/D used is the stock solution described in example 7. The corresponding recovery yields obtained are given in table 10. In both cases, a high recovery yield is got for the elution with water.

TABLE 10 recovery yields of the elution of IFN-B/D for various chromatography media (the washing buffer is 0.1M TRIS-HCl pH 7.6)

| chromatography media | base matrix of the gel | % eluted with washing buffer | % eluted with H$_2$O | % eluted with 2M NH$_4$Cl |
|---|---|---|---|---|
| Chelating-Sepharose Fast Flow ® | agarose | 0 | 89 | 11 |
| TSK Toyopearl AF-Chelate-650 M ® | type "vinyl polymer" | 0 | 100 | 0 |

DEPOSITION OF MICROORGANISMS

The following microorganism strains were deposited at the Deutsche Sammiung von Mikroorganismen (DSM), Mascheroder Weg 1B, D-38142 Braunschweig, Germany (accession numbers and deposition dates given):

*Saccharomyces cerevisiae* HT 393
DSM 9697 Jan. 27, 1995

We claim:

1. A process for the enrichment of an impure or pre-purified protein comprising the steps:
   a) adsorbing of the impure or pre-purified protein on immobilized copper(II) ions,
   b) washing of the adsorbed protein with a solution of a Lewis-base, and
   c) eluting the desired protein with deionized water.

2. A process according to claim 1 wherein the Lewis-base solution contains NH$_4^+$ or a primary, secondary or ternary amine in a neutral or low alkaline pH region or OH$^-$ at a high alkaline pH region.

3. A process according to claim 1 wherein the Lewis-base solution contains NH$_4^+$ or a primary amine.

4. A process according to claim 1 wherein the Lewis-base solution contains OH$^-$ in a buffered pH region of 9–11.

5. A process according to claim 1 wherein the Lewis base is selected from the group consisting of ethanolamine, cystine, NH$_4$SCN, NH$_4$Cl, NH$_4^+$CH$_3$COO$^-$, (NH$_4$)$_2$SO$_4$ and TRIS-HCl.

6. A process according to claim 1 wherein the Lewis-base is used in a concentration of 0.001 to 1 M.

7. A process according to claim 1 wherein the deionized water does not contain more than 0.001 M ionic compounds.

8. A process according to claim 1 wherein the Lewis-base does not destroy totally a complex between said protein and copper(II) ions.

9. A process according to claim 1 wherein the impure or pre-purified protein is interferon, amylase, trypsin or a related protein.

10. A process according to claim 1 wherein the impure or pre-purified protein is selected from the group consisting of interferon-α, trypsin and α-amylase.

11. A process according to claim 1 wherein the deionized water contains non-ionic compounds.

12. A process according to claim 1 wherein the deionized water contains sugar or polyol.

13. A process according to claim 1 wherein the deionized water contains mannitol or glycerol.

14. A process according to claim 1 wherein the adsorbing of the protein on immobilized copper(II) ions and washing with a solution of a Lewis-base are carried out simultaneously.

15. A process according to claim 1 wherein the adsorbed protein is washed with a buffer that is not a Lewis-base, or with both a buffer that is not a Lewis-base and with deionized water prior to washing with a solution of a Lewis-base.

16. A process according to claim 1 wherein the copper(II) ions are immobilized on a stationary support.

17. A process according to claim 16 wherein the stationary support is agarose or a vinyl polymer.

18. A process according to claim 1 wherein the Lewis-base solution contains NH$_4^+$ or a primary, secondary or ternary amine.

19. A process according to claim 18 wherein the Lewis-base is adjusted to pH 6–9.

20. A process according to claim 1 wherein the Lewis-base solution contains one or more additional salts that are not Lewis-bases.

21. A process according to claim 20 wherein the additional salt is NaCl or KCl.

22. A process according to claim 20 wherein the additional salt is used in a concentration of up to 5 M.

23. A process according to claim 20 wherein the additional salt is used in a concentration of up to 2 M.

* * * * *